United States Patent [19]

Vinci et al.

[11] Patent Number: 5,391,788
[45] Date of Patent: * Feb. 21, 1995

[54] PRODUCTION OF HIGH PURITY FATTY ACID SALT PRODUCTS

[75] Inventors: Alfredo Vinci, Dayton; Ronald L. Forrest, Cranbury, both of N.J.

[73] Assignee: Church & Dwight Co., Inc., Princeton, N.J.

[*] Notice: The portion of the term of this patent subsequent to May 18, 2010 has been disclaimed.

[21] Appl. No.: 52,265

[22] Filed: Apr. 23, 1993

Related U.S. Application Data

[63] Continuation-in-part of Ser. No. 52,264, Apr. 23, 1993.

[51] Int. Cl.$^6$ .............................................. C07C 51/00
[52] U.S. Cl. ..................................... 554/156; 426/74; 426/507
[58] Field of Search ........................... 426/74; 584/156

[56] References Cited

U.S. PATENT DOCUMENTS

| | | | |
|---|---|---|---|
| 5,212,325 | 5/1993 | Lajore | 554/156 |
| 5,215,768 | 6/1993 | Vince et al. | 426/74 |

*Primary Examiner*—José G. Dees
*Assistant Examiner*—Deborah D. Carr
*Attorney, Agent, or Firm*—Charles B. Barris

[57] ABSTRACT

The present inventions provides a process for preparing a $C_{14}$–$C_{22}$ fatty acid alkaline earth metal salt product which is essentially free of $C_{14}$–$C_{22}$ fatty acid or $C_{14}$–$C_{22}$ fatty acid glyceride. The glyceride content of $C_{14}$–$C_{22}$ fatty acid starting material is hydrolyzed with a water-soluble basic compound such as sodium carbonate in the first step of the process. The $C_{14}$–$C_{22}$ fatty acid salt aqueous dispersion formed in the first step is converted to an alkaline earth metal salt in a subsequent process step. A biologically active constituent such as methionine hydroxy analog can be incorporated as an additional ingredient during the processing.

12 Claims, No Drawings

PRODUCTION OF HIGH PURITY FATTY ACID SALT PRODUCTS

REFERENCE TO RELATED PATENT APPLICATION

The present patent application is a continuation-in-part of patent application Ser. No. 08/052,264, filed Apr. 23, 1993.

BACKGROUND OF THE INVENTION

Conventional cattle feeds such as corn and alfalfa often fail to provide sufficient energy for cattle, especially lactating dairy cattle during periods of heavy milk production. Feed containing a high proportion of corn also has a tendency to depress the milk fat content of the milk produced by such cattle. Fat is an excellent energy source, and it is known that if the proportion of fat in cattle food is increased, lactating dairy cattle produce high milk yields without draining their reserves of body fat and without diminishing the proportion of milk fat in the milk produced.

However, it has been found that if the proportion of fat in the diet of cattle exceeds about 2% of the total feed solids, the feed has toxic effects upon the microorganisms in the rumen of the cattle. It appears that fat reduces the growth rate or even kills certain microorganisms which digest fiber in the cow's rumen, thereby lowering fiber digestibility. This deleterious effect on the cow's rumen is particularly true of unsaturated fats. Although the decreased fiber digestion in the rumen is partially compensated by greater fiber digestion in the lower parts of the alimentary canal, such later fiber digestion produces a blend of different fatty acids than that which is produced by the digestion in the rumen, and the different blend of fatty acids is less suited to the cow's metabolism.

It is known also that triglycerides and free fatty acids can physically coat fibrous or cellulosic material in the rumen and inhibit fermentation of the material by the bacteria. This has an adverse effect on the total digestibility of the diet, and can result in a reduced yield of milk and butter-fat.

There has been a continuing need for new dietary supplements for animal feedstuff which can be fed to ruminant animals without interfering with feed metabolism by rumen microorganisms.

U.S. Pat. Nos. 4,642,317; 4,826,694; 4,853,233; and 4,909,138 describe the incorporation of insoluble fatty acid salts in ruminant feed as a means of increasing the fat content of the feed without deleteriously affecting the ruminant digestion cycle. A feed additive such as fatty acid calcium salt functions as a rumen bypass product, and is subsequently metabolized in the abomasum or small intestine of the ruminant.

Accordingly, it is an object of this invention to provide a process for the production of a fatty acid salt composition which contains little or no free fatty acid or fatty acid glyceride, and which can function as a rumen bypass animal feed supplement and promote a beneficial increase in the dietary fat content of the feed.

It is another object of this invention to provide a process for converting an impure fatty acid mixture into a particulate fatty acid salt product which consists essentially of fatty acid calcium salts, and which contains no free fatty acid or fatty acid glyceride constituents.

It is a further object of this invention to provide a process for the preparations of an animal feed supplement product which comprises a high purity fatty acid calcium salt ingredient, in combination with a biologically active ingredient.

Other objects and advantages of the present invention shall become apparent from the accompanying description and examples.

DESCRIPTION OF THE INVENTION

One or more objects of the present invention are accomplished by the provision of a process for the preparation of a fatty acid salt product which comprises (1) forming a reactive admixture of ingredients comprising (a) $C_{14-22}$ fatty acid having about 2–40 weight percent of the $C_{14-22}$ fatty acid content in glyceride form, (b) basic alkali metal or ammonium compound, and (c) aqueous medium, and conducting the reaction for a period sufficient to hydrolyze the glyceride constituent to $C_4$–$C_{22}$ fatty acid and glycerol, and to form an aqueous dispersion of $C_4$–$C_{22}$ fatty acid salt; (2) forming a reactive admixture of ingredients comprising (a) $C_{14}$–$C_{22}$ fatty acid salt aqueous dispersion from step (1), and (b) between about 0.8–1.4 equivalents of water-soluble alkaline earth metal compound per equivalent of $C_{14}$–$C_{22}$ fatty acid salt; and (3) recovering $C_{14}$–$C_{22}$ fatty acid alkaline earth metal salt product after completion of a salt-forming reaction in step (2), wherein the salt product has a content of free $C_{14}$–$C_{22}$ fatty acid or $C_{14}$–$C_{22}$ fatty acid glyceride respectively less than about one weight percent, based on the weight of $C_{14}$–$C_{22}$ fatty acid content.

The $C_{14}$–$C_{22}$ fatty acid alkaline earth metal salt content of an invention salt product typically is at least about 80 weight percent of the salt product weight, and is essentially free of unreacted $C_{14}$–$C_{22}$ fatty acid $C_{14}$–$C_{22}$ fatty acid glyceride constituents.

The invention process can be conducted by reacting a salt-forming alkaline earth metal compound with a step (1) aqueous dispersion mixture of saturated and unsaturated carboxylic acid compounds, such as those derived from vegetable oils and animal tallow.

Palm fatty acid distillate is a commercial product produced by distilling the fatty acids present in natural palm oil. A distillate product typically has the following weight percent content:

| | |
|---|---|
| Free fatty acids | 60–90 |
| Water | <1 |
| Triglycerides | 10–40 |
| Unsaponifiables | <3 |

The iodine value is less than 54 and the melting point is about 45° C. The content of peroxides is below 10 milliequivalents of oxygen per kilogram.

The fatty acids in the free fatty acids and the triglycerides can consist of the following weight percent:

| | | preferred |
|---|---|---|
| Palmitic acid | 20–60 | 30–50 |
| Oleic acid | 25–60 | 30–40 |
| Linoleic acid | 2–20 | 5–10 |
| Stearic acid | 1–15 | 2–10 |
| Lauric acid | 0–10 | 1–5 |

Beef tallow acids are available commercially as a byproduct obtained by alkaline extraction of waste beef fat and subsequent acidification, and normally contain the following weight percent of fatty constituents:

| Free fatty acids | 60–90 |
|---|---|
| Triglycerides | 10–40 |
| Water | <1 |
| Unsaponifiables | <3 |

The iodine is less than 50 and the melting point is 40°–45° C. The content of peroxides is less than 10 milliequivalents of oxygen per kilogram. The fatty acids in the free fatty acids and in the triglycerides can have the following weight percent content:

| Palmitic acid | 20–30 |
|---|---|
| Oleic acid | 35–45 |
| Linoleic acid | 2–10 |
| Stearic acid | 15–25 |

The term "glyceride" as employed herein includes fatty acid monoglycerides, diglycerides and triglycerides, and any mixture thereof.

Because unsaturated fatty acids are susceptible to atmospheric oxidation, it is advantageous to incorporate an oil-soluble antioxidant, and a chelating agent to bind any ferric, copper, zinc or other metal capable of catalyzing atmospheric oxidation. Suitable quantities for inclusion in the fatty acid bulk are about 0.03–0.1% or higher of antioxidant as permitted by regulation, and about 0.05–0.3% of chelating agent, based on the weight of fatty acid.

Illustrative of preferred additives are butylated hydroxytoluene antioxidant, and citric acid and ethylenediamine tetracetate chelating agents. The chelating agent is added in an edible solvent such as propylene glycol to facilitate blending into the fatty acid.

The alkali metal or ammonium compound ingredient in step (1) of the invention process preferably is utilized in a quantity which is at least one base equivalent per acid equivalent of $C_{14}$–$C_{22}$ fatty acid and $C_{14}$–$C_{22}$ fatty acid glyceride constituents of the reactive admixture. The quantity of alkali metal or ammonium compound normally is at least sufficient to convert the total content of free fatty acid and fatty acid glyceride into a salt derivative.

Suitable alkali metal or ammonium compounds for step (1) of the process include water-soluble sodium, potassium and ammonium compounds or any mixture therefore selected from bicarbonates, carbonates, phosphates and hydroxides.

The step (1) reaction is conducted for a period of about 0.1–1.5 hours, and the reaction temperature is maintained in the range of about 30°–110 C.

It is convenient to add the basic alkali metal or ammonium compound as a 10–60 weight percent solution in the aqueous medium ingredient in step (1) of the process. The neutralization of the free $C_{14}$–$C_{22}$ fatty acid constituent proceeds readily at ambient temperature when the basic reagent solution is added. Hydrolysis of the $C_{14}$–$C_{22}$ fatty acid glyceride content can be accelerated by raising the reaction admixture temperature to about 60°–110 C.

The quantity of $C_{14}$–$C_{22}$ fatty acid derivative formed in step (1) comprises about 20–70 weight percent, based on the weight of aqueous dispersion. The pH of the aqueous dispersion in step (1) normally is in the range of about 7–10.5.

The water-soluble alkaline earth metal ingredient in step (2) of the process is at least one member selected from a group of compounds which includes calcium chloride, calcium nitrate, calcium formate, calcium acetate, magnesium chloride, magnesium nitrate, magnesium sulfate, magnesium formate and magnesium acetate.

The term "water-soluble" as employed herein refers to an alkaline earth metal compound which has a solubility of at least about 10 grams per 100 grams of water at 25° C.

The salt-forming reaction temperature in step (2) of the process can be in the range of about 30°–110° C., and the reaction period can vary in the range of about 0.3–2 hours.

The amount of aqueous medium present in step (2) is sufficient to support the alkaline earth metal compound dissolution and fatty acid salt-forming reaction, and preferably is vaporized as steam during the exothermic reaction period to yield a friable fatty acid salt product which in granule form is suitable for use as an animal feed supplement.

The $C_{14}$–$C_{22}$ fatty acid alkaline earth metal salt product recovered in step (3) of the process can have a content of basic alkali metal or ammonium byproduct, depending on the method of recovery. Optionally, an alkali metal compound byproduct such as sodium chloride can be removed by slurrying the fatty acid alkaline earth metal salt product in an aqueous medium at ambient temperature for a period of about 0.1–1 hour. The purified fatty acid alkaline earth metal salt product (at least 90 percent purity) can be recovered by filtration or centrifugation, and dried to a desired level of water content.

In a further embodiment of the present invention between about 0.05–20 weight percent of a biologically active constituent, based on the weight of $C_{14}$–$C_{22}$ fatty acid ingredient, is incorporated as an additional ingredient during the processing to prepare a $C_{14}$–$C_{22}$ fatty acid alkaline earth metal salt product.

The optional biologically active ingredient can be selected from a broad variety of nutrients and medicaments, either as a single component or as a mixture of components, which are illustrated by the following listing of active molecular species:

1. $C_2$–$C_{22}$ aliphatic carboxylic acids and esters, and alkali metal, ammonium and alkaline earth metal salts which are different than the selected $C_{14}$–$C_{22}$ fatty acid ingredient of the process.
2. sugars and complex carbohydrates which include both water-soluble and water-insoluble monosaccharides, disaccharides and polysaccharides.

Cane molasses is a byproduct from the extraction of sucrose from sugar cane. It is commercially available at standard 79.5° Brix concentration, which has a water content of about 21 weight percent, and a sugar content of 50 weight percent. Sugar beet byproducts also are available as low cost carbohydrate sources.

Whey is a byproduct of the dairy industry. The whey is a dilute solution of lactalbumin, lactose, fats, and the soluble inorganics from milk. Dried whey solids typically have the following composition:

| Protein | 12.0% |
|---|---|
| Fat | 0.7% |
| Lactose | 60.0% |
| Phosphorus | 0.79% |
| Calcium | 0.87% |

| | |
|---|---|
| -continued | |
| Ash | 9.7% |

Another source of carbohydrate is derived from the pulp and paper industry which produces large quantities of byproduct lignin sulfonates from wood during the sulfite pulping process. The byproduct is recovered in the form of salts such as ammonium, sodium and magnesium lignin sulfonates.

3. aminoacid ingredients either singly or in combination which include arginine, histidine, isoleucine, leucine, lysine, methionine, phenylalanine, threonine, tryptophan, valine, tyrosine ethyl HCl, alanine, aspartic acid, sodium glutamate, glycine, proline, serine, cysteine ethyl HCl, and the like, and analogs thereof.
4. vitamin ingredients either singly or in combination which include thiamine HCl, riboflavin, pyridoxine HCl, niacin, inositol, choline chloride, lecithin, calcium pantothenate, biotin, folic acid, ascorbic acid, vitamin $B_{12}$, p-aminobenzoic acid, vitamin A acetate, vitamin K, vitamin D, vitamin E, and the like.

Trace element ingredients include compounds of cobalt, copper, manganese, iron, zinc, tin, nickel, chromium, molybdenum, iodine, chlorine, silicon, vanadium, selenium, calcium, magnesium, sodium and potassium.

5. protein ingredients are obtained from sources such as dried blood or meat meal, cottonseed meal, soy meal, dehydrated alfalfa, dried and sterilized animal and poultry manure, fish meal, liquid or powdered egg, fish solubles, cell cream, rape seed oil (canola oil), defatted rape seed, and the like.

Protein equivalent ingredients include non-protein nitrogen compounds such as urea, biuret, ammonium phosphate, and the like.

6. medicament ingredients either singly or in combination which include promazine hydrochloride, chloromadionate acetate, chlorotetracycline, sulfamethazine, monensin, sodium monensin, poloxaline, and the like. Oxytetracycline is a preferred antibiotic for cattle prophylaxis.
7. enzymes such as lipolytic proteins which aid feed digestibility, e.g., by hydrolysis of fatty acid glycerides to free fatty acid and glycerol.

The biologically active ingredient can be premixed with the $C_{14}$-$C_{22}$ fatty acid or with the aqueous medium, as facilitated by the fat-solubility or water-solubility of the biologically active ingredient.

It is preferred that a fatty acid alkaline earth metal salt dietary supplement product produced by an invention process embodiment has little or no detectable unpleasant odor. Optionally, an odor-modifying compound can be added to the product to mask any residual odor.

It is advantageous to include one or more additives which impart improved flavor and aroma to an invention fatty acid salt product. Flavorant additive can be categorized as natural, artificial and WONF (with other natural flavorants), and can be added in a quantity between 0.0001–2 weight percent, based on the weight of fatty acid calcium salt ingredient.

Suitable flavorant additives which exhibit flavor and aroma enhancing organoleptic properties generally are organic compounds which correspond to structure classifications such as aliphatic and aromatic alcohols, furan ethers, thiazole alcohols, pyridine ethers and alcohols, benzofuran carbonyl compounds, aliphatic and aromatic ketones, $\alpha$-diketones, pyrrole-$\alpha$-diketones, aromatic sulfur compounds, phenols and phenol ethers, and the like, as recited in U.S. Pat. No. 3,702,253.

Flavorant additives are illustrated by compounds such as anethole, benzaldehyde, bergamot oil, acetoin, carvol, cinnamaldehyde, citral, ethylvanillin, vanillin, thymol, methyl salicylate, coumarin, anise, cinnamon, ginger, clove, lemon oil, 1-undecanol, 5-dodecalactone, eugenol, geraniol, geranyl acetate, guaiacol, limonene, linalool, piperonal, 2-acetyl-5-methylpyrazine, 2-ethyl-3-methoxypyrazine 5-methylquinoxaline, 2-methyl-6-propylpyrazine, 2-methylbenzofuran, 2,2'-dithienylmethane, benzyl hexyl carbinol, furfuryl phenyl ether, difurfuryl ether, benzofuran-2-aldehyde, benzothiophene-2-aldehyde, 1-butylpyrrole-2-aldehyde, methyl decyl ketone, dipropyl ketone, ethyl benzyl ketone, 2,6-diacetylpyridine, heptane-3,4-dione, methyl thiophene-2-carboxylate, 2-hydroxyacetophenone, 4-ethyl-2-methoxyphenol, 2-oxobutan-1-ol, and the like.

A present invention fatty acid salt product is adapted to function as a rumen bypass dietary supplement in ruminant feed. An important advantage of a present invention dietary supplement composition is the rumen bypass protection which extends to all the biologically active ingredients of the composition, which normally are metabolized in the rumen.

The following Examples are further illustrative of the present invention. The components and specific ingredients are presented as being typical, and various modifications can be derived in view of the foregoing disclosure within the scope of the invention.

EXAMPLE I

This Example illustrates the production of fatty acid salt with a reduced content of free fatty acid and glyceride in accordance with the present invention.

The fatty acid component is a palm fatty acid distillate of the following composition:

| | |
|---|---|
| Lauric acid | 2.3% |
| Palmitic acid | 49.9% |
| Stearic acid | 5.4% |
| Oleic acid | 35.0% |
| Linoleic acid | 7.4% |

About 15 weight percent of the fatty acid is in the form of glyceride ester.

Palm fatty acid distillate (760 g) is charged to a reactor. The reactor contents are stirred while a 30 weight percent aqueous solution of 50/50 sodium carbonate/potassium carbonate is added dropwise. The addition is continued until the quantity of basic salt in the reaction medium is about equivalent to the total equivalence of fatty acid and fatty acid glyceride reactants.

The stirred reaction medium is heated to 60° C., and maintained for a reaction period of 1.5 hours. The reaction medium is cooled to room temperature, and the resultant fatty acid salt aqueous dispersion has a pH of 7.6. The fatty acid salt content of the aqueous dispersion is about 55 weight percent.

Calcium chloride (190.g) is added to the reactor contents of fatty acid salt aqueous dispersion with stirring. The reactor is heated as required to maintain a reaction medium temperature of about 100° C.

Steam evolves during the exothermic calcium chloride dissolution and fatty acid calcium salt-forming reaction, and after a reaction period of about 2 hours the final product is in the form of a friable solid.

The final product has a fatty acid calcium salt content of about 80 weight percent, a water content of about 6 weight percent, and is essentially free of fatty acid and fatty acid glyceride content.

The process is repeated, except that methionine hydroxy analog sodium salt (30 g) and soy lecithin (20 g) are blended with the fatty acid salt aqueous dispersion before the calcium chloride addition step.

EXAMPLE II

This Example illustrates the continuous production of fatty acid calcium salt with a reduced content of free fatty acid and glyceride in accordance with the present invention.

The fatty acid component is a palm fatty acid distillate of the following composition:

| Lauric acid | 2.3% |
|---|---|
| Palmitic acid | 49.9% |
| Stearic acid | 5.4% |
| Oleic acid | 35.0% |
| Linoleic acid | 7.4% |

About 15 weight percent of the fatty acid is in the form of glyceride ester.

A reserve supply of fatty acid salt aqueous dispersion is prepared following the procedures and utilizing the material balances described in Example I. The fatty acid salt content of the aqueous dispersion is about 60 weight percent.

The process is operated continuously with equipment which is essentially the same as described and illustrated with reference to FIG. 1 of U.S. Pat. No. 4,826,694 by W. McAskie.

Calcium nitrate from a hopper and hot fatty acid salt aqueous dispersion (90° C.) from a supply line are mixed in predetermined proportions in a mixing pump (1.1 equivalents of calcium nitrate per equivalent of fatty acid salt).

The hydrated mixture is passed through a mixing pump and the resultant semi-liquid reaction medium at about 100° C. is discharged as a spread layer onto a continuously moving conveyor belt. Steam evolves from the conveyor transported reaction mass.

At the end of the conveyor belt, solid lumps of reaction product fall through a sizing machine onto a second conveyor belt. In this conveying zone the salt-forming reaction and evolution of water proceed to completion. The essentially dry fatty acid calcium salt product is passed through a sifter, and collected in bags suitable for transportation and storage.

The residence time on the first conveyor is about 45 minutes, and the overall production time from reactant mixing to collection of the dry granulated product is about 3 hours.

The final product has a fatty acid calcium salt content of 82 weight percent, a water content of about 3 weight percent, and is essentially free of fatty acid and fatty acid glyceride content.

What is claimed is:

1. A process for the preparation of a fatty acid salt product which comprises (1) forming a reactive admixture of ingredients comprising (a) $C_{14}$–$C_{22}$ fatty acid having about 2–40 weight percent of the $C_{14}$–$C_{22}$ fatty acid content in glyceride form, (b) basic alkali metal or ammonium compound, and (c) aqueous medium, and conducting the reaction for a period sufficient to hydrolyze the glyceride constituent to $C_{14}$–$C_{22}$ fatty acid and glycerol, and to form an aqueous dispersion of $C_4$–$C_{22}$ fatty acid salt; (2) forming a reactive admixture of ingredients comprising (a) $C_{14}$–$C_{22}$ fatty acid salt aqueous dispersion from step (1), and (b) between about 0.8–1.4 equivalents of water-soluble alkaline earth metal compound per equivalent of $C_4$–$C_{22}$ fatty acid salt; and (3) recovering $C_4$–$C_{22}$ fatty acid alkaline earth metal salt product after completion of a salt-forming reaction in step (2), wherein the salt product has a content of free $C_{14}$–$C_{22}$ fatty acid or $C_4$–$C_{22}$ fatty acid glyceride respectively less than about one weight percent, based on the weight of $C_{14}$–$C_{22}$ fatty acid content.

2. A process in accordance with claim 1 wherein the $C_4$–$C_{22}$ fatty acid ingredient, in step (1) comprises at least two $C_4$–$C_{22}$ fatty acid constituents.

3. A process in accordance with claim 1 wherein the fatty acid ingredient in step (1) is a mixture comprising 0–10 percent lauric acid, 0–60 percent palmitic acid, 0–15 percent stearic acid, 0–60 percent oleic acid, and 0–20 percent linoleic acid, in the form of free fatty acids and fatty acid glycerides.

4. A process in accordance with claim 1 wherein the quantity of alkali metal or ammonium compound ingredient in step (1) is at least one equivalent per equivalent of $C_{14}$–$C_{22}$ fatty acid and $C_{14}$–$C_{22}$ fatty acid glyceride.

5. A process in accordance with claim 1 wherein the alkali metal or ammonium compound ingredient is step (1) is a water-soluble sodium, potassium or ammonium compound or any mixture thereof selected from bicarbonates, carbonates, phosphates and hydroxides.

6. A process in accordance with claim 1 wherein the reaction period in step (1) is about 0.1–1.5 hours, and the reaction temperature is about 30°–110° C.

7. A process in accordance with claim 1 wherein the quantity of $C_{14}$–$C_{22}$ fatty acid salt derivative formed in step (1) comprises about 20–70 weight percent, based on the weight of aqueous dispersion.

8. A process in accordance with claim 1 wherein the pH of the aqueous dispersion in step (1) is in the range of about 7–10.5.

9. A process in accordance with claim 1 wherein the alkaline earth metal compound in step (2) is selected from calcium chloride, calcium nitrate, magnesium chloride, magnesium sulfate and magnesium nitrate.

10. A process in accordance with claim 1 wherein the salt-forming reaction temperature in step (2) is about 30°–110° C., and the reaction period is about 0.3–2 hours.

11. A process in accordance with claim 1 wherein water evaporation occurs during the salt-forming reaction in step (2) and the salt product is recovered in the form of friable granules.

12. A process in accordance with claim 1 wherein a biologically active constituent is incorporated as an additional ingredient during the processing.

* * * * *

UNITED STATES PATENT AND TRADEMARK OFFICE
CERTIFICATE OF CORRECTION

PATENT NO. : 5,391,788
DATED : February 21, 1995
INVENTOR(S) : Alfredo Vinci, et al It is certified that error appears in the above-indentified patent and that said Letters Patent is hereby corrected as shown below:

Column 2, lines 18 and 19, on each line "$C_4$-$C_{22}$" should be -- $C_{14}$-$C_{22}$ --.

Column 8, lines 9, 14, 15, 18, 22 and 23, on each line "$C_4$-$C_{22}$" should be -- $C_{14}$-$C_{22}$ --.

Signed and Sealed this

Sixth Day of June, 1995

BRUCE LEHMAN

*Commissioner of Patents and Trademarks*